United States Patent [19]

Greenshields

[11] Patent Number: 4,770,871

[45] Date of Patent: Sep. 13, 1988

[54] PROCESS FOR THE PREPARATION OF DIANHYDROSORBITOL ETHERS

[75] Inventor: James N. Greenshields, Wilmington, Del.

[73] Assignee: ICI Americas Inc., Wilmington, Del.

[21] Appl. No.: 117,293

[22] Filed: Nov. 6, 1987

[51] Int. Cl.$^4$ .......................... A61K 7/16; A61K 9/68
[52] U.S. Cl. ........................................ 424/49; 424/48; 424/464; 549/464; 514/469
[58] Field of Search ..................................... 424/48–58, 424/464; 549/464

[56] References Cited

U.S. PATENT DOCUMENTS 4,585,649 4/1986 Lynch .................................... 424/49

Primary Examiner—J. R. Brown
Assistant Examiner—F. T. Moezie

[57] ABSTRACT

A blend of mono- and dialkyl-1,4:3,6-dianhydrosorbitol is made by alkylation of 1,4:3,6-dianhydrosorbitol with dialkyl carbonate in the presence of a base catalyst. Mono- and dialkylated blends obtained therefrom are useful in plaque inhibiting dentrifice compositions.

9 Claims, No Drawings

PROCESS FOR THE PREPARATION OF DIANHYDROSORBITOL ETHERS

Mono- and diethers of 1,4:3,6-dianhydrosorbitol (also known as isosorbide) having the following general formula

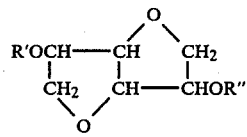

when incorporated with dentifrice formulations, described in U.S. Pat. No. 4,585,649, act to reduce irritation and plaque accumulation caused by plaque forming organisms such as *Streptococcus mutans*. Such dentifrice formulations include mouthwash, mouthspray, toothpaste, toothdrops, toothgels, chewing gums, confections, toothpicks, dental floss, lip creams and the like. In view of this important personal hygiene application, there is need for an inexpensive process for the preparation of these dianhydrosorbitol ethers. The present invention is directed to an improved high yield process for manufacturing etherified dianhydrosorbitol using dialkyl carbonate as the alkylating agent for isosorbide.

It has now been discovered that isosorbide and monoalkylisosorbide may be readily alkylated at high conversion rates with dialkyl carbonates at elevated temperatures and pressures in the presence of a base catalyst. The process is relatively economic in that products may be obtained in high yields using available alkylation and distillation equipment. Unlike conventional alkylating agents, such as alkyl halides and dialkyl sulphates, dialkyl carbonates react to give only volatile by products, specifically an alcohol and carbon dioxide. Thus, it is not necesssary to employ the filtration and extraction stages associated with the removal of inorganic salts after the use of conventional alkylation agents. Dialkyl carbonates are, therefore, more readily adapted for use in a continious alkylation process.

The alkyl carbonates employed as the alkylating agent has the general formula R'OCOOR" wherein R' and R" may be individually selected from the group consisting of —$CH_3$, —$C_2H_5$, —$C_3H_7$, —$C_4H_9$ and mixtures thereof.

Examples of organic carbonates which may be employed are dimethyl carbonate, ethylmethyl carbonate, diethyl carbonate, propylmethyl carbonate, isopropylmethyl carbonate, isopropylethyl carbonate, butylmethyl carbonate, secondary-butylmethyl carbonate, isobutylmethyl carbonate, tertiary-butylmethyl carbonate, cyclohexylmethyl carbonate, dipropyl carbonate, dibutyl carbonate and diallyl carbonate. Preferred organic carbonates include dimethyl and diethyl carbonate.

The process may be carried out batchwise, continuously or semibatchwise or semicontinuously. When the organic carbonate is a liquid under the conditions of the reaction, it often acts as the solvent for isosorbide. In the case of manufacturing dimethylisosorbide and methyisosorbide the use of dimethylisosorbide as a reaction solvent is advantageous in that it is recovered with the product. In general, any higher boiling solvent may be employed which is inert to the reaction ingredients. When a solvent is needed, only that amount sufficient to provide a uniform dispersion of ingredients is used.

The temperature at which the reaction is carried out can be varied depending on the carbonate, the catalyst and reaction pressure. Normally the reaction may be carried out in temperatures ranging from 90° C. to about 300° C. Preferably the reaction temperature used is about 200° C. and most preferably in the range of 240°–260° C.

The reaction is normally carried out under autogeneous pressure, which can be as high as 5 megapascals gauge. Lower pressures can be used by the selective removal of one or more by-products.

The reaction is conducted in the presence of a base catalyst. Preferably the base employed is an organic amine compound and preferably a tertiary amine compound. Such amines can be in the form of solids or liquids and in some instances a quatenary ammonium or amine-containing resin is employed. Other conventional base materials such as alkali metal alkoxides, carbonates, hydroxides and amides can be used. Such basic catalysts may be selected from pyridine, 4-(dimethylamino)pyridine, imidazole, 2,6-lutidine, 2,4,6-collidine, and diazobicyclo octane.

Dianhydrosorbitol (isosorbide) is the product resulting from the removal of two molecules of water from sorbitol, a 6 carbon straight chain hexahydric alcohol. The removal of two molecules of water from a hexitol results in the formation of isohexide which is a diinnerether such as isosorbide, isomanide or isoidide. The process of the invention includes all of these materials. However, the most useful material known at this time is isosorbide, which is commercially available or easily made from the dianhydridization of sorbitol.

In carrying out the reaction, isosorbide may react with either one or two mols of alkyl carbonate to form either the mono- or diether of isosorbide with either one or two mols of the corresponding alkyl alcohol and one or two mols of carbon dioxide. In general, the greater the molar excess of alkyl carbonate employed in the reaction with respect to isosorbide, the more complete is the dietherification of isosorbide. Usually a 3–10 mol excess is used. The conversion also is dependent upon the concentration of catalysts which may range from about 0.1–3% by weight based on the weight of isosorbide in the reaction mix. The conversion rate also is dependent upon the temperature and pressure employed in carrying out the reaction. Conversions approaching 90% are obtained at 250° C. at about 4 megapascals when methyl carbonate is used. The reaction may be driven to further completion by periodically venting carbon dioxide and other by-products from the reactor.

Etherified products of isosorbide having formula I wherein R' and R" may individually be selected from the group consisting of —$CH_3$, —$C_2H_5$, —$C_3H_7$ and —$C_4H_9$ and alternatively —H when the other R' or R" is an alkyl group of 1–4 carbon atoms. The compounds made by the invention specifically include methylisosorbide, dimethylisosorbide, ethylisosorbide, diethylisosorbide, propylisosorbide, dipropylisosorbide, monoisopropylisosorbide, diisopropylisosorbide, methylethylisosorbide, methylpropylisosorbide, ethylpropylisosorbide, butylisosorbide, dibutylisosobide, isobutylisosorbide, diisobutylisosorbide, methylbutylisosorbide, ethylbutylisosorbide, propylbutylisosorbide and the equivalent isomanide and isoidide modifications.

Most often in the practice of the invention the dialkyl carbonate is used to produce the equivalent dialkyl or monoalkyl isosorbide derivative. However, when the process is employed to manufacture active ingredients for use as dentifrice and pharmaceutical compositions, it appears that mixtures of the methyl-, dimethyl-, ethyl-, diethyl, propyl-, and dipropylisosorbides can be used effectively and need not be purified by procedures other than by simple purification by distillation to remove starting materials and catalysts. In the case where volatile catalysts are employed, they may be converted to easily removable salts by the addition of small amounts of neutralizing acids. Normally unreacted starting materials are recovered and recycled. In some cases a certain portion of the higher boiling component from a previous run may be employed as solvent for a future run such that additional carbonate and isosorbide are further reacted therein in a semibatch or semicontinuous operating procedure. In a fully continuous operation, the alkyl carbonate/isosorbide or monoalkylisosorbide is passed either over a catalytic resin packed column or in solution with base catalyst at the reaction temperature to form by-products and higher boiling residue which is continuously transferred to a pressurized multi-plate distillation column to remove several streams containing $CO_2$, alkyl alcohol, product and residues. In a batchwise procedure, all the reaction ingredients are placed in an autoclave, heated to the appropriate reaction temperature and thereafter vented to remove volatiles which are condensed and separated by simple distillation procedures. Atmospheric and lower temperature techniques may be employed in a homogeneous catalytic solution such that carbon dioxide and alkyl alcohol are continuously removed to drive the reaction to completion.

The process of the invention may be further understood by reference to the following nonlimiting examples wherein all proportions are expressed on a weight basis unless otherwise specified.

EXAMPLES 1-4

Into sealed glass Carius tubes were placed dimethyl carbonate (DMC), isosorbide (IS), and small amounts of catalysts selected from 1,4-diazobicyclo[2,2,2]octane (DABCO), dimethylaminopyridine (DMAP) and sodium methoxide. The glass tubes were placed in a protective autoclave for 2 hours and thereafter cooled to room temperature. The residues were analyzed by gas chromatographic technique. Yields are expressed in area percentages. Molar proportions and yields of dimethylisosorbide (DMI) and monomethylisosorbide (MMI) are presented in the following table.

TABLE 1

| Example | Moles DMC Per Mol IS | Temp C.° | Catalyst (wt. %) | Conversion of IS.W % | Wt./Wt. DMI: | Ratio of MMI |
|---|---|---|---|---|---|---|
| 1 | 3 | 250 | DABCO (1.0) | 89 | 59 | 41 |
| 2 | 6 | 200 | DABCO (1.0) | 59 | 29 | 71 |
| 3 | 3 | 200 | DMAP (0.36) | 72 | 46 | 54 |
| 4 | 3 | 200 | NaOMe (2) | 52 | 50 | 50 |

The DMI/MMI blend obtained by removal of starting materials and by-products made by the process of Example 1 can be effectively employed in the manufacture of a conventional toothpaste having a formula similar to that of Table II. The blend is expected to perform as well in other personal hygiene applications mentioned above.

TABLE II

| Ingredients | Parts by Wt. | | |
|---|---|---|---|
| Dimethylisosorbide (DMI/MMI) | 10 | 25 | 50 |
| Cellulose gum, CMC-7MF | 1.25 | 1.25 | 1.25 |
| Glycerine | 5.0 | 5.0 | 5.0 |
| Magnesium Aluminum silicate | 0.25 | 0.25 | 0.25 |
| 70% Sorbitol Solution USP | 30.0 | 30.0 | 30.0 |
| Dicalcium phosphate dihydrate | 28.0 | 28.0 | 28.0 |
| Dicalcium phosphate (Anhydrous) | 20.0 | 20.0 | 20.0 |
| Sodium Lauryl Sulfate | 1.0 | 1.0 | 1.0 |
| Sodium Saccharine | 0.2 | 0.2 | 0.2 |
| Flavor | q.s | q.s | q.s |
| Water | q.s | q.s | q.s |

The above ingredients are formulated into a workable toothpaste by first dispersing the above quantities of ingredients as follows: cellulose gum is dispersed in glycerine. The Magnesium Aluminum sulfate is dispersed in water under high shear. These two components are mixed with the DMI/MMI blend of Example 1 and sorbitol solution and thereafter with the remaining ingredients listed above. Water is then added in a conventional mixer to obtain the desired paste viscosity.

What is claimed is:

1. A process for the preparation of etherified dianhydrosorbitol having the following formula I

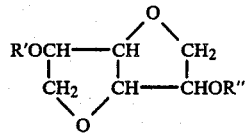

wherein R' and R" are individually alkyl radicals selected from the group consisting of —$CH_3$, —$C_2H_5$, —$C_3H_7$, —$C_4H_9$ or —H when one of R' or R" is an alkyl group of 1-4 carbon atoms which comprises reacting isosorbide with at least quantitative amounts of dialkyl carbonate having the formula R'OCOOR" wherein R' and R" are alkyl groups described above in the presence of catalytic amounts of base at temperatures ranging from 90°-300° C.

2. A process of claim 1 wherein the molar ratio of dialkyl carbonate to isosorbide ranges from 1-10.

3. A process of claim 1 wherein the reaction is carried out at 200°-300° C. at elevated pressure.

4. A process of claim 1 wherein the reaction is carried out with from 0.1-3 weight percent based on the weight of isosorbide of an organic amines.

5. A process of claim 1 which is carried out in solvent solution.

6. A process of claim 5 wherein said solvent is dimethyl isosorbide.

7. A blend of dialkyl- and monoalkylisosorbide made by the process of claim 1 when separated from the reaction by-products and starting materials.

8. A dentifrice composition which contains a plaque reducing effective amount of a product of claim 7.

9. A dentifrice of claim 8 in the form of mouthwash, toothpaste, mouthspray, toothdrops, chewing gum, soft candy, toothpicks, dental floss and lip creams.

* * * * *